United States Patent [19]

Schwindeman

[11] Patent Number: 4,707,180

[45] Date of Patent: Nov. 17, 1987

[54] HERBICIDALLY ACTIVE ISOXAZOLYL-IMIDAZOLIDINONE DERIVATIVES

[75] Inventor: James A. Schwindeman, Fairlawn, Ohio

[73] Assignee: PPG Industries, Inc., Pittsburgh, Pa.

[21] Appl. No.: 744,728

[22] Filed: Jun. 14, 1985

[51] Int. Cl.4 .................... A01N 43/50; C07D 233/22
[52] U.S. Cl. ....................................... 71/92; 548/245; 548/246
[58] Field of Search ............... 548/245, 246, 317, 318, 548/319; 71/92

[56] References Cited

U.S. PATENT DOCUMENTS 4,345,936  8/1982  Thibault et al. ..................... 548/319
4,354,030 10/1982  Barow et al. ....................... 548/247

FOREIGN PATENT DOCUMENTS 2881  7/1979  European Pat. Off. ................ 71/92
2543552 10/1984  France ................................... 71/92

OTHER PUBLICATIONS

Hatzios, et al., *Metabolism of Herbicides in Higher Plants*, Burgess, Minneapolis (1982) p. 5.
Ariens, E. J., *Drug. Design*, vol. II, Academic Press, New York (1971) p. 76.

Primary Examiner—Donald G. Daus
Assistant Examiner—Barbara Cassatt
Attorney, Agent, or Firm—Edward J. Whitfield

[57]  ABSTRACT

The invention relates to certain 3-isoxazolyl-2-imidazolidinone derivatives, namely 3-[5- or 3-substituted-3- or -5-isoxazolyl]-1-substituted-4- or 5-substituted amino-2-imidazolidinones and the use thereof for pre-emergence or postemergence control of noxious plants, i.e., weeds.

4 Claims, No Drawings

HERBICIDALLY ACTIVE ISOXAZOLYL-IMIDAZOLIDINONE DERIVATIVES

FIELD OF THE INVENTION

This invention relates to certain 3-isoxazolyl-2-imidazolidinone derivatives, namely 3-[5- or 3-substituted-3- or -5-isoxazolyl-1-substituted-4- or 5-substituted amino-2-imidazolidinones and the use thereof for preemergence or postemergence control of noxious plants, i.e., weeds.

DESCRIPTION OF THE INVENTION

This invention provides herbicidally active 3-[5- or 3-substituted-3- or -5-isoxazolyl]-1-substituted-4- or 5-substituted amino-2-imidazolidinones represented by the Formula I:

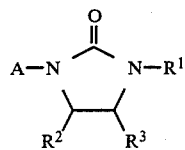   I.

wherein A is

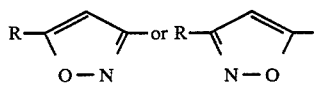

wherein:
R is up to $C_6$ alkyl, haloalkyl or cycloalkyl, up to $C_5$ alkenyl or alkynyl; —$R^4$—O—$R^5$ or —$R^4$—S—$R^5$ wherein $R^4$ is up to $C_6$ alkylene and $R^5$ is up to $C_6$ alkyl or optionally substituted phenyl or benzyl; $R^1$ is up to $C_3$ alkyl or allyl; $R^2$ and $R^3$ are selected from hydrogen, hydroxy or —$NR^6R^7$ with the proviso that one of $R^2$ or $R^3$ must —$NR^6R^7$, wherein $R^6$ is selected from hydrogen or up to $C_6$ alkyl or haloalkyl; and $R^7$ is

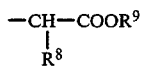

wherein $R^8$ is selected from hydrogen, up to $C_6$ alkyl or haloalkyl, aryl or substituted aryl; and $R^9$ is selected from alkali metal, hydrogen, up to $C_6$ alkyl, haloalkyl or alkoxyalkyl, phenyl or substituted phenyl.

The compounds of this invention can be synthesized using available starting materials, such as the isoxazolyl-imidazolidinone compounds described in U.S. Pat. No. 4,268,679 and using techniques known to the art. For example, certain of the compounds of this invention may be prepared by reacting an isoxazolyl-imidazolidinone compound of the formula:

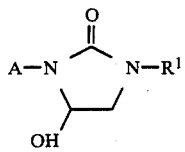

wherein A and $R^1$ are as previously defined, with a suitably substituted amine of the formula, $NHR^6R^7$ wherein $R^6$ and $R^7$ are as previously defined. The reaction is typically conducted in an inert organic solvent medium at up to reflux temperature and usually in the presence of a strong mineral or organic acid, e.g., p-toluenesulfonic acid.

The following Examples are illustrative of the preparation of certain compounds of this invention.

EXAMPLE I

Preparation of: 3-[5-(t-butyl)-3-isoxazolyl]-1-methyl-4-(N-carboethoxymethyl)amino-2-imidazolidinone To a 500 milliliter flask provided with a magnetic stirring bar, Dean-Stark trap and a reflux condenser were charged 19.0 grams (0.0794 mole) of 3[5-(t-butyl)-3-isoxazolyl]-1-methyl-4-hydroxy-2-imidazolidinone and 200 milliliters of dry toluene. This slurry was warmed on a steam bath until all of the solid dissolved. 18 grams (0.175 mole) of carboethyoxymethyl amine dissolved in 20 milliliters of dry toluene was added followed by 1.07 grams of p-toluenesulfonic acid. The reaction mixture was heated to reflux and maintained at reflux until HPLC analysis indicated complete conversion of starting materials. The reaction mixture was then cooled, transferred to a separatory funnel, diluted with 300 milliliters of ethyl acetate and washed with 300 milliliters of saturated aqueous sodium bicarbonate. The aqueous layer was drawn-off and extracted with 2×200 milliliter portions of ethyl acetate. The combined organic layers were dried over anhydrous magnesium sulfate, filtered and concentrated in vacuo affording 25.68 grams of reddish-orange oil confirmed by NMR analysis as the desired product.

EXAMPLE II

Preparation of: 3-[5-(t-butyl)-3-isoxazolyl]-1-methyl-4-(N carbomethoxymethyl)amino-2-imidazolidinone To a 100 milliliter flask provided with a magnetic stirring bar, a Dean-Stark trap and a reflux condenser were charged 7.17 grams (0.05 mole) of 3-[5-(t-butyl)-3-isoxazolyl]-1-methyl-4-hydroxy-2-imidazolidinone, and 40 milliliters of dry toluene. The mixture was heated via an oil bath until all of the solid dissolved. To the hot, yellow solution were added 3.8 grams (0.044 mole) of carbomethoxymethylamine and 0.52 grams of p-toluenesulfonic acid. The reaction was heated to reflux and maintained at reflux until TLC analysis indicated complete consumption of starting material. The reaction mixture was cooled, transferred to a separatory funnel, diluted with 100 milliliters of ethyl acetate and washed with a 120 milliliter portion of saturated aqueous sodium bicarbonate. The organic layer was washed with 100 milliliters of saturated brine and dried by filtering through a cone of anhydrous magnesium sulfate. The crude material was recrystallized from chloroform/hexane and solvent was removed in vacuo from the filtrate. The residue was digested with diethylether, concentrated to about 40 milliliters and cooled in an ice bath. The white precipitate was removed by filtration and the filtrate as stripped of solvent affording 7.4 grams of a golden oil confirmed by NMR analysis as the desired product.

EXAMPLE III

Preparation of:
3-[5-(t-butyl)-3-isoxazolyl]-1-methyl-4-[N-(1-carboethoxy)ethyl]amino-2-imidazolidinone To a 100 milliliter flask provided with a magnetic stirring bar, a Dean-Stark trap and reflux condenser were charged 4.78 grams (0.02 mole) of 3-[5-(t-butyl)-3-isoxazolyl]-1-methyl-4-hydroxy-2-imidazolidinone, and 20 milliliters of dry toluene. The mixture was heated via an oil bath to effect dissolution, after which were added 5.3 grams (0.0453 mole) of N-(1-carboethoxy)ethyl amine and 0.31 gram of p-toluenesulfonic acid. The reaction mixture was heated via the oil bath to 120° C. and maintained at that temperature for eight hours. After cooling to room temperature, HPLC analysis indicated that conversion of starting material was not quite complete, so heating at 120° C. was continued for another 16 hours. After cooling HPLC analysis indicated complete conversion of starting material. The reaction mixture was transferred to a separatory funnel, diluted with 100 milliliters of ethyl acetate and washed consecutively with 100 milliliter portions of saturated sodium bicarbonate and sodium chloride solutions. The organic layer was dried over anhydrous magnesium sulfate, filtered and concentrated in vacuo affording 6.45 grams of an orange oil confirmed by NMR analysis as the desired product.

Although the invention has been illustrated by the foregoing Examples with regard to the preparation of certain compounds within the scope of Formula I, it is to be understood that other compounds within the scope of Formula I may readily be prepared by those skilled in the art simply by varying the choice of starting materials and using the same or similar techniques.

Weed control in accordance with this invention is effected by applying to the soil prior to emergence of weeds therefrom or to the plant surfaces subsequent to emergence from the soil, a herbicidally effective amount of a compound of this invention. It is, of course, to be understood that the term "a pound of this invention" also includes mixtures of such compounds or a formulation containing a compound or mixture of compounds of this invention.

The term "herbicidally effective amount" is that amount of a compound of this invention required to so injure or damage weeds such that the weeds are incapable of recovering following application while not causing substantial injury to any valuable crop amongst which the weeds might be growing. The quantity of compound of this invention applied in order to exhibit a satisfactory herbicidal effect may vary over a wide range and depends on a variety of factors, such as, for example; hardiness of a particular weed species, extent of weed infestation, climatic conditions, soil conditions, method of application, and the like. Typically, as little as one or less pound or acre of a compound of this invention would be expected to provide satisfactory weed control, although in some instances application rates in excess of one pound per acre, e.g., up to 5 or more pounds per acre might be required. Of course, the efficacy of a particular compound against a particular weed species may readily be determined by routine laboratory or field testing in a manner well known to the art. It is expected that satisfactory weed control can be had at a rate of application in the range of 0.1 to 1.0 pound per acre.

Of course, a compound of this invention can be formulated according to routine methods with any of several known and commonly used herbicidal diluents, adjuvants and carriers. The formulations can contain liquid carriers and adjuvants such as organic solvents, as well as emulsifiers, stabilizers, dispersants, suspending agents, spreaders, penetrants, wetting agents and the like. Typical carriers utilized in dry formulations include clay, talc, diatomaceous earth, silica and the like. Preferred formulations are those in the form of wettable powders, flowables, dispersible granulates or aqueous emulsifiable concentrates which can be diluted with water at the site of application. Also, dry formulations such as granules, dusts, and the like, may be used.

When, desired, a compound of this invention can be applied in combination with other herbicidal agents in an agents in an effort to achieve even broader vegetative control. Typical herbicides which can be conveniently combined with Formula I compound include atrazine, hexazinone, metribuzin, ametryn, cyanazine, cyprazine, prometon, prometryn, propazine, simazine, terbutryn, propham, alachlor, acifluorfen, bentazon, metalachlor and N,N-dialkyl thiocarbamates such as EPTC, butylate or venolate. These, as well as other herbicides described, for example, in the *Herbicide Handbook of the Weed Science Society of America*, may be used in combination with a compound or compounds of the invention. Typically such formulations will contain from about 5 to about 95 percent by weight of a compound of this invention.

The herbicidally formulations contemplated herein can be applied by an of several method known to the art. Generally, the formulation will be surfaced applied as an aqueous spray. Such application can be carried about by conventional ground equipment, or if desired, the sprays can be aerially applied. Soil incorporation of such surface applied herbicides is accomplished by natural leaching, and is of course facilitated by natural rainfall and melting snow. If desired, however, the herbicides can be incorporated into the soil by conventional tillage means.

Compounds of this invention are believed effective for emergence of postemergence control of a wide variety of broadleaf and grassy weeds. Typical of the various species of vegetative growth that may be controlled, combated, or eliminated are, for example, annuals such as pigweed, lambsquarters, foxtail, crabgrass, wild mustard, field pennycress, ryegrass, goose grass, chickweed, wild oats, velvetleaf, purslane, barnyardgrass, smartweed, knotweed, cocklebur, kochia, medic, ragweed, hemp nettle, spurrey, pondweed, carpetweed, morningglory, ducksalad, cheatgrass, fall panicum, jimsonweed, witchgrass, watergrass, wild turnip, and similar annual grasses and weeds. Biennials that may be controlled include wild barley, campion, burdock, bull thistle, roundleaved mallow, purple star thistle, and the like. Also controlled by the compounds of this invention are perennials such as quackgrass, Johnsongrass, Canada thistle, curley dock, field chickweed, dandelion, Russian knapweed aster, horsetail, ironweed, sesbania, cattail, wintercress, horsenettle, nutsedge, milkweed, sicklepod, and the like.

The compounds prepared as described in the Examples were individually tested for herbicidal efficacy against a variety of broadleaf and grassy weed species, under controlled laboratory conditions of light, humidity and temperature. Solvent solutions of said compounds were applied, both preemergence and postemergence, to test flats containing the various weed species, and herbicidal efficacy was evaluated vis a vis an untreated control, by periodic visual inspection after application of the compounds. Herbicidal efficacy was evaluated on a Numerical Injury Rating (NIR) scale of from 0 (no injury) to 10 (all plants dead). A NIR rating of 7-9 indicates severe injury; a NIR rating of 4-6 indicates moderate injury, i.e., plant growth is reduced to the extent that normal growth would be expected only under ideal conditions; and a NIR rating of 1-5 indicates slight injury.

The following table give the average preemergence and postemergence NIR determined for each of the compounds prepared as described in Examples I through III on the broadleaf (BL) and grassy (GR) weed species to which the compounds were applied. Each compound was applied at a rate of 0.5 pound per acre rate and the NIR was determined two weeks subsequent to application.

|  | I | II | III |
|---|---|---|---|
| Pre-BL | 9.8 | 10 | 10 |
| Pre-GR | 9.2 | 8.3 | 10 |
| Post-BL | 9.4 | 9.2 | 9.8 |
| Post-GR | 6.5 | 6.5 | 7.0 |

The broadleaf weeds used in the screening tests were coffeeweed, jimsonweed, tall morningglory, teaweed, wild mustard and velvetleaf. The grassy weeds used in the screening tests were barnyardgrass, large crabgrass, Johnsongrass, wild oats and yellow foxtail.

Although the invention has been described in considerable detail by the foregoing, it is to be understood that many variations may be made therein by those skilled in the art without departing from the spirit and scope thereof as defined by the appended claims.

I claim:

1. A compound of the formula:

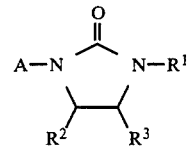

wherein A is

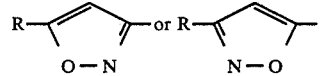

wherein:
R is up to $C_6$ alkyl, haloalkyl or cycloaklyl, up to $C_5$ alkenyl or alkynyl; $-R^4-O-R^5$ or $-R^4-S-R^5$ wherein $R^4$ is up to $C_6$ alkylene and $R^5$ is up to $C_6$ alkyl or phenyl or benzyl;
$R^1$ is up to $C_3$ alkyl or allyl;
$R^2$ and $R^3$ are selected from hydrogen, hydroxy or $-NR^6R^7$ with the proviso that one of $R^2$ or $R^3$ must be $-NR^6R^7$, wherein $R^6$ is selected from hydrogen or up to $C_6$ alkyl or haloalkyl; and $R^7$ is

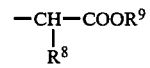

wherein $R^8$ is selected from hydrogen, up to $C_6$ alkyl or haloalkyl, phenyl or benzyl; and $R^9$ is selected from alkali metal, hydrogen, up to $C_6$ alkyl, haloalkyl or alkoxyalkyl, phenyl.

2. A compound of claim 1 selected from 3-[5-(t-butyl)-3isoxazolyl]-1-methyl-4-(N-carboethoxymethyl-)amino-2-imidazolidinone; 3-[5-(t-butyl)-3-isoxazolyl]-1-methyl-4-(N-carbomethyoxymethyl)amino-2imidazolidinone; or 3-[5-(t-butyl)-3-isoxazolyl]-1-methyl-4-[N-(1carboethoxy)ethyl]amino-2-imidazolidinone.

3. A herbicidal composition containing an inert carrier and a herbicidally effective amount of a compound or mixture of compounds defined in claim 1.

4. The method of controlling the growth of weeds wherein a herbicidally effective amount of herbicide is applied to a growth medium prior to emergence of weeds therefrom or to the weeds subsequent to emergence from the growth medium wherein the improvement resides in using as the herbicide a compound or mixture of compounds as defined in claim 1.

* * * * *